United States Patent [19]

Sturdivant

[11] 4,412,821
[45] Nov. 1, 1983

[54] DENTAL MOUTH MIRROR

[76] Inventor: Jack E. Sturdivant, Oakwood Rd., Rte. #4, Ames, Iowa 50010

[21] Appl. No.: 401,651

[22] Filed: Jul. 26, 1982

[51] Int. Cl.³ .............................................. A61B 1/24
[52] U.S. Cl. .................................................... 433/30
[58] Field of Search .............................. 433/29, 30, 31

[56] References Cited
U.S. PATENT DOCUMENTS

| | | | |
|---|---|---|---|
| 1,493,909 | 5/1924 | Vandiver | 433/29 |
| 3,171,203 | 3/1965 | Arroyo | 433/31 |
| 3,599,334 | 8/1971 | Warden | 433/31 |

Primary Examiner—Robert Peshock
Attorney, Agent, or Firm—Zarley, McKee, Thomte, Voorhees & Sease

[57] ABSTRACT

A dental mouth mirror is disclosed herein comprising a substantially flat plate means having a mirrored upper surface. An arcuate indentation is formed in the posterior edge of the plate means and posterior lobe portions appear at opposite ends of the arcuate indentation. The anterior edge portion of the plate means is comprised of an outwardly extending arcuate portion. Arcuate indentations are formed in the opposite side edges of the plate means forming anterior lobe portions at the ends of the anterior edge portion.

6 Claims, 4 Drawing Figures

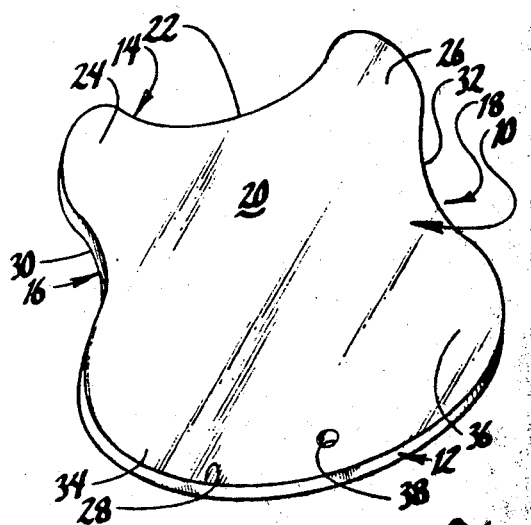
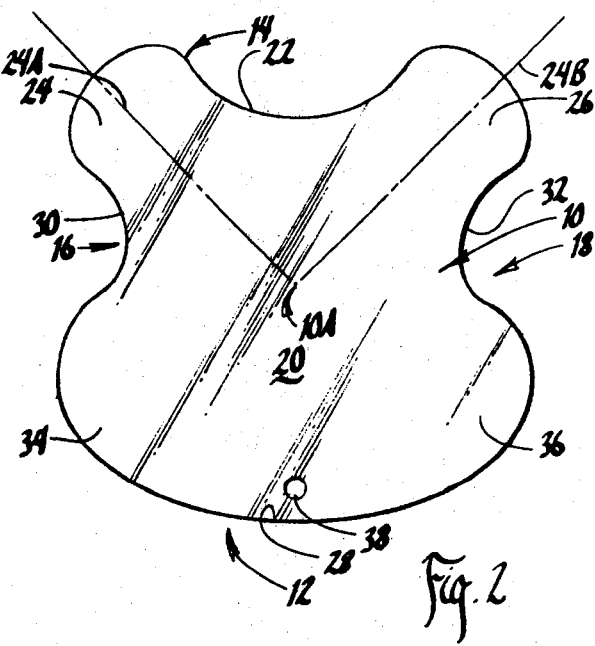
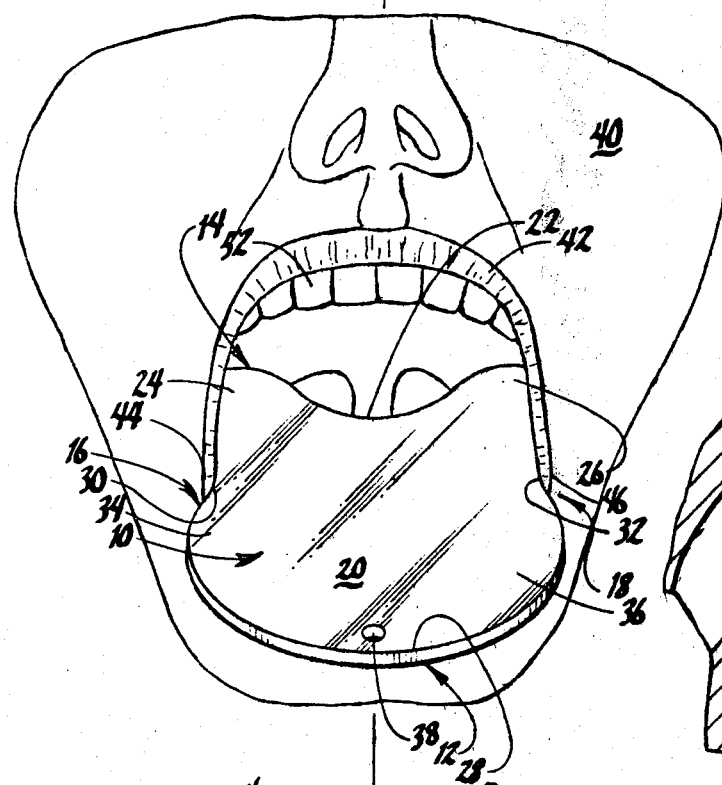
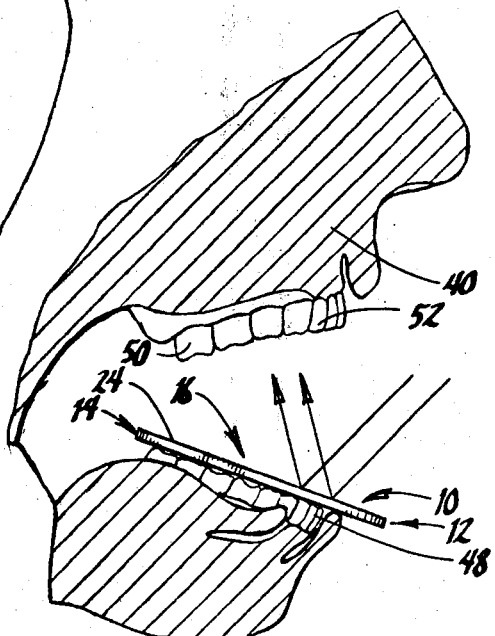

DENTAL MOUTH MIRROR

BACKGROUND OF THE INVENTION

While installing upper interior orthodontic brackets, it is necessary to sight from the incisal edge to the long axis of the tooth of the upper incisors and cuspids in order to properly position and align the orthodontic brackets. A right-handed person, for example, can position the brackets with his right hand while holding a conventional dental hand mirror in his other hand. However, both the right and left hand are often needed for installation of the brackets, and the manual holding of the mirror is therefore often greatly inconvenient.

Brackets for holding dental mirrors have been previously used, but they often impede the work on the patient and in some cases are uncomfortable for the patient.

It is therefore the purpose of this invention to provide a dental mirror which is entirely supported by the mouth of the patient.

It is a further object of this invention to provide a dental mirror which is rounded outwardly at its anterior edge to provide a view of the upper anterior teeth.

It is a further object of this invention to provide a dental mirror with lateral projections or lobes so that the buccal or posterior teeth will be in view when looking downward on the mirror.

It is a further object of this invention to provide a dental mirror with an indentation in the osterior edge to allow for the tongue position of the patient.

It is a further object of this invention to provide an aperture adjacent the anterior edge portion of the mirror whereby dental floss or the like can be used for additional securement purposes if necessary.

A further object of the invention is to provide a dental mirror that is comfortable to the patient as it is fully supported by the patient's mouth.

These and other objects will be apparent to those skilled in the art.

BRIEF SUMMARY OF THE INVENTION

The dental mouth mirror of this invention comprises a substantially flat plate means having a mirrored upper surface. The plate means is comprised of a plastic material and has opposite side edges and anterior and posterior edge portions. An arcuate indentation is located in the posterior edge portion and in between two posterior lobe portions. The anterior edge portion of the plate means comprises an outwardly extending arcuate position.

Arcuate indentations are formed in the opposite side edges of the plate means to form anterior lobe portions at the ends of the anterior edge portion.

An aperture is placed in the plate means adjacent the anterior edge portions to accommodate dental floss or the like if additional securement means is desired. An anti-fogging material can be placed on the mirror to prevent fogging of the mirror from the breath of the patient.

BRIEF DESCRIPTION OF THE DRAWINGS

FIG. 1 is an upper perspective view of the device of this invention;

FIG. 2 is a top plan view thereof;

FIG. 3 is a perspective view of the device of this invention located in the mouth of a dental patient;

FIG. 4 is a sectional view of the device of this invention taken on line 4—4 of FIG. 3.

DESCRIPTION OF THE PREFERRED EMBODIMENT

The numeral 10 designates the flat plastic plate means which comprises the dental mouth mirror of this invention. Plate means 10 has a geometric center 10A. The plate means is flat and relatively thin in construction and includes an outer or anterior edge portion 12, an inner or posterior edge portion 14, and side edge portions 16 and 18. The plate means 10 includes a mirrored upper surface 20. The material of this dental mirror is available on the market, and does not per se, comprise a part of this invention.

The posterior edge portion 14 includes an arcuate indentation 22 which accommodates the tongue position of the patient. Arcuate lobes 24 and 26 appear at opposite ends of the arcuate indentation 22. The lobes 24 and 26 enable the dentist to have a full view of the buccal or posterior teeth. The center axes 24A and 26A of lobes 24 and 26, respectively, even generally outwardly and rearwardly from the geometric center 10A of plate means 10. The radius of curvature of indentation 22 is greater than the radius of curvature of lobes 24 and 26. Similarly, the lateral span of indentation 11 is greater than the lateral width of lobes 24 and 26.

The anterior edge portion 12 is arcuate in shape and extends outwardly from the center of the plate means 10 to enable the dentist to have a view of the upper anterior teeth when viewing the mirror.

Arcuate indentations 30 and 32 appear in the side edge portions 16 and 18, respectively, to create rounded anterior lobes 34 and 36 at the end of the anterior edge portion 12.

The lateral width of plate means 10 measured across the posterior lobes 24 and 26 is substantially the same as the corresponding distance measured across anterior lobes 34 and 36.

An aperture 38 extends through the plate means 10 adjacent the anterior edge portion 23. The aperture 38 is used to receive dental floss or the like in the event that there is some need to provide additional securing means for the mirror in the mouth of the patient.

The numeral 40 designates the patient having a mouth 42. The corners of the mouth are designated by the numerals 44 and 46. The numeral 48 designates the lower incisors and the numerals 50 and 52 designate the patient's posterior and anterior teeth, respectively.

The device of this invention fits just over the lower incisors 48 and rests comfortably in the corners 44 and 46 of the mouth as the corners 44 and 46 are received in the indentations 30 and 32 of the plate means 10.

All of the edges of the plate means 10 are rounded to insure the comfort of the patient. For almost all uses, the resiliency of the patient's mouth firmly holds the plate means in position. In those instances where additional securement is necessary, dental floss or the like can be threaded through the aperture 38 and secured to other appendages in the mouth of the patient.

Any conventional anti-fogging material can be placed on the mirrored surface 20 to prevent any condenstation from the breath of the patient appearing thereon.

This mirror is comfortable to the patient and provides the dentist with a full view of both the patient's upper anterior and posterior teeth. Further, the mirror of this invention frees both hands of the dentist to use in the function being undertaken.

From the foregoing, it is seen that the device of this invention will achieve at least all of its stated objectives.

I claim:

1. A dental mouth mirror, comprising:

a substantially flat plate means having a mirrored upper surface, opposite side edges, and anterior and posterior edge portions, tion, arcuate posterior lobe portions adjacent opposite edges of said first arcuate indentation, said posterior lobe portions adapted to extend into the open mouth of a dental patient, said first arcuate indentation having a radius of curvature greater than the radius of curvature of said lobe portions wherein the lateral span of said arcuate indentation is greater than the lateral width of said lobe portions, said anterior edge portion comprising an outwardly extending arcuate portion, second arcuate indentations in said opposite side edges forming anterior lobe portions with the end of said outwardly extending arcuate portion, said second arcuate indentations being adapted to receive the corners of the mouth of a dental patient to secure the mirror in the open mouth of such patient.

2. The dental mouth mirror of claim 1 wherein said plate means has a geometric center, and said lobe portions have center axes that extend outwardly and rearwardly from said geometric center.

3. The dental mouth mirror of claim 1 wherein the lateral width of said plate means measured across said posterior lobe portions is substantially equal to the lateral width of said plate means measured across said anterior lobe portions.

4. The dental mouth mirror of claim 1 wherein an anti-fogging material is placed on said mirrored upper surface.

5. The dental mouth mirror of claim 1 wheein said plate means is comprised of a plastic material.

6. The dental mouth mirror of claim 1 wherein an aperture extends through said plate means adjacent said anterior edge portion.

* * * * *